United States Patent
Shibata et al.

(10) Patent No.: US 10,195,162 B2
(45) Date of Patent: Feb. 5, 2019

(54) TOLTERODINE-CONTAINING ADHESIVE PATCH

(71) Applicant: TEIKOKU SEIYAKU CO., LTD., Kagawa (JP)

(72) Inventors: Taiki Shibata, Kagawa (JP); Kensuke Murata, Kagawa (JP); Kenichi Hattori, Kagawa (JP); Shinji Tanaka, Kagawa (JP)

(73) Assignee: TEIKOKU SEIYAKU CO., LTD., Kagawa (JP)

( * ) Notice: Subject to any disclaimer, the term of this patent is extended or adjusted under 35 U.S.C. 154(b) by 0 days.

(21) Appl. No.: 14/368,320

(22) PCT Filed: Dec. 25, 2012

(86) PCT No.: PCT/JP2012/083400
§ 371 (c)(1),
(2) Date: Jun. 24, 2014

(87) PCT Pub. No.: WO2013/099835
PCT Pub. Date: Jul. 4, 2013

(65) Prior Publication Data
US 2015/0017226 A1    Jan. 15, 2015

(30) Foreign Application Priority Data
Dec. 27, 2011 (JP) ................. 2011-286530

(51) Int. Cl.
| A61K 9/70 | (2006.01) |
|---|---|
| A61K 31/70 | (2006.01) |
| A61K 31/137 | (2006.01) |
| A61K 31/7076 | (2006.01) |
| A61K 31/7084 | (2006.01) |

(52) U.S. Cl.
CPC .......... A61K 31/137 (2013.01); A61K 9/7053 (2013.01); A61K 31/70 (2013.01); A61K 31/7076 (2013.01); A61K 31/7084 (2013.01)

(58) Field of Classification Search
None
See application file for complete search history.

(56) References Cited

U.S. PATENT DOCUMENTS

| 5,242,984 | A | * | 9/1993 | Dillman et al. ............... 525/314 |
| 5,885,565 | A | * | 3/1999 | Elias .................... A61K 9/0014 424/433 |
| 6,517,864 | B1 | | 2/2003 | Orup Jacobsen et al. |
| 6,783,769 | B1 | | 8/2004 | Arth et al. |
| 2006/0029673 | A1 | | 2/2006 | Breitenbach et al. |
| 2007/0077282 | A1 | | 4/2007 | Shirai et al. |
| 2009/0075860 | A1 | * | 3/2009 | Yamaguchi .......... A61K 9/0014 514/1.1 |
| 2009/0297591 | A1 | | 12/2009 | Chiang et al. |
| 2010/0331552 | A1 | | 12/2010 | Hwang et al. |
| 2013/0053357 | A1 | * | 2/2013 | Kuma et al. .................. 514/171 |
| 2013/0195957 | A1 | | 8/2013 | Shinoda et al. |
| 2015/0030666 | A1 | | 1/2015 | Ogino et al. |

FOREIGN PATENT DOCUMENTS

| JP | 2002-523446 | 7/2002 |
|---|---|---|
| JP | 2002-544222 | 12/2002 |
| JP | 2004-284953 | 10/2004 |
| JP | 2006-522759 | 10/2006 |
| JP | 2011-512405 | 4/2011 |
| JP | 2011-521975 | 7/2011 |
| WO | 2000/12070 | 3/2000 |
| WO | 02/05790 | 1/2002 |
| WO | 2009/104920 | 8/2009 |
| WO | 2009/146443 | 12/2009 |
| WO | WO-2011-136283 | * 11/2011 |
| WO | 2012/017892 | 2/2012 |
| WO | 2013/081014 | 6/2013 |

OTHER PUBLICATIONS

International Search Report dated Mar. 19, 2013 issued in corresponding International Application No. PCT/JP2012/083400.
Notification of Transmittal of Translation of the International Preliminary Report on Patentability dated Jul. 10, 2014 issued in corresponding International Application No. PCT/JP2012/083400.
Hiroshi Mizumachi, "Handbook of Pressure Sensitive Adhesive Technology", 1997, pp. 353-367 (with partial English translation).
Extended European Search Report dated Apr. 21, 2015, issued in corresponding European Patent Application No. 12861215.7.

* cited by examiner

*Primary Examiner* — Aradhana Sasan

(74) *Attorney, Agent, or Firm* — Wenderoth, Lind & Ponack, L.L.P.

(57) ABSTRACT

The present invention provides a tolterodine-containing patch in which an adhesive layer is laminated on a backing, characterized in that the adhesive layer is obtainable by adding tolterodine to an adhesive base comprising a rubber adhesive, a tackifier resin, and a softener, wherein the tolterodine is present in the form of a free base in the adhesive base.

13 Claims, No Drawings

TOLTERODINE-CONTAINING ADHESIVE PATCH

TECHNICAL FIELD

The present invention relates to an improved tolterodine-containing patch which shows excellent transdermal absorbability, excellent drug stability during storage, and low skin irritation.

BACKGROUND ART

Tolterodine is used in the treatment of hyperactive bladder, and widely distributed in the market in the form of an oral formulation. Currently, a commercially available tolterodine oral formulation mainly uses tolterodine tartrate as an active ingredient.

Meanwhile, regarding a transdermal absorption-type formulation containing tolterodine, there have been attempts to develop a patch by various methods until now (Patent Documents 1-4). A patch has advantages, for example, in that a constant blood drug concentration can be maintained and the administration can easily be discontinued by peeling off the patch when a side effect occurs. Further, while an oral formulation requires a liquid such as water at the time of administration and thus has a possibility of producing an adverse effect on the treatment due to increase of urge to urinate, a patch does not increase urge to urinate and thus is advantageous to drug compliance of a patient.

Generally, in a transdermal absorption-type formulation, it is known that higher transdermal absorbability is achieved when a free base is used as compared to an acid addition salt. Therefore, regarding tolterodine, mainly a patch using a free base has been reported (Patent Documents 2-4).

However, if an inappropriate base ingredient is selected for a patch using a tolterodine free base, tolterodine may react with the base ingredient and thereby may be decomposed. As a result, the content of the active ingredient may decrease during storage, a degradation product may be produced, and thereby an adverse effect may occur in the formulation stability. Namely, if a tolterodine free base is selected as the active ingredient, an appropriate base ingredient must be selected so as not to produce an adverse effect in the active ingredient stability.

The patch containing a tolterodine free base disclosed in the above Patent Documents 2-4 mainly uses an acrylic adhesive. However, when tolterodine is mixed with an acrylic adhesive, the content of the active ingredient decreases during storage, and a degradation product is readily formed. Namely, in view of the formulation stability, a patch containing an acrylic adhesive as a base ingredient is insufficient.

Also, a tolterodine-containing patch has a problem with skin irritation. In this respect, the present inventors have found that a transdermal permeation rate of tolterodine (flux: $\mu g/cm^2/hr$) is correlated with the skin irritation of a patch. Therefore, in the preparation of a tolterodine-containing patch, the present inventors have found that a good balance between drug efficacy and safety can be achieved by adjusting the transfer rate of the drug from a formulation to a skin in an appropriate range. These properties of tolterodine are not described nor suggested in the above related art documents, and are newly found by the present inventors' earnest studies.

RELATED ART DOCUMENTS

Patent Documents

Patent Document 1: JP 2011-512405 A
Patent Document 2: JP 2002-523446 A
Patent Document 3: JP 2002-544222 A
Patent Document 4: JP 2011-521975 A

SUMMARY OF THE INVENTION

Problems to be Solved by the Invention

In the currently-known tolterodine-containing patch, a tolterodine free base is used to increase the transdermal absorbability of the drug. However, when a tolterodine free base is used, tolterodine may react with a base ingredient and thereby its stability may decrease, and tolterodine may be decomposed to produce its degradation product. Furthermore, a tolterodine-containing patch has a problem of skin irritation etc.

Means for Solving the Problems

The present invention solves the above problems in the tolterodine-containing patch, and provides an improved tolterodine-containing patch in which the transdermal absorbability of the active ingredient is excellent, the drug stability during storage is excellent, and the skin irritation is decreased.

Namely, the present invention relates to a tolterodine-containing patch in which an adhesive layer is laminated on a backing, characterized in that the adhesive layer is obtainable by adding tolterodine as an active ingredient to an adhesive base comprising a rubber adhesive, a tackifier resin, and a softener, wherein the tolterodine is present in the form of a free base in the adhesive base.

Also, a more specific aspect of the present invention provides a tolterodine-containing patch in which the transdermal permeation rate of tolterodine (flux: $\mu g/cm^2/hr$) in a steady state is in the range of 1.0-50.0.

Effect of the Invention

According to the present invention, a patch in which the transdermal absorbability and the stability of tolterodine are excellent, and the skin irritation is decreased can be provided by adding tolterodine to an adhesive base comprising a rubber adhesive, a tackifier resin, and a softener, wherein the tolterodine is present in the form of a free base in the adhesive base.

MODE FOR CARRYING OUT THE INVENTION

A tolterodine-containing patch of the present invention can be prepared by using an adhesive base comprising a rubber adhesive, a commonly-used tackifier resin and a softener, adding tolterodine as an active ingredient thereto to obtain a composition for an adhesive layer, and then laminating it on a backing.

In the tolterodine-containing patch of the present invention, the amount of the tolterodine free base is 0.5-20% by weight, preferably 1-10% by weight on the basis of the total weight of the adhesive layer. When the amount of the tolterodine free base is less than 0.5% by weight, a sufficient drug efficacy cannot be obtained. Meanwhile, when the amount is greater than 20% by weight, an adverse effect may occur on the physical properties of the formulation, and the cost-effectiveness decreases. Further, regarding the tolterodine of the present invention, a tolterodine free base may be added, or an acid addition salt of tolterodine such as tolterodine tartrate may be added at the beginning, and then a basic compound such as sodium hydroxide or an amine is added thereto to eliminate the addition salt to produce a tolterodine free base in the formulation. As the basic compound, an amine is preferable, and diethanolamine is especially preferable. As the amount of the basic compound, 0.3-13% by weight on the basis of the total weight of the adhesive layer is preferable, and 0.6-6.5% by weight is especially preferable. The ratio (molar ratio) of the amount of an acid addition salt of tolterodine and the amount of a basic compound, i.e., "basic compound/acid addition salt of tolterodine" is 0.8-5.0, preferably 1.0-3.0.

Also, in the tolterodine-containing patch of the present invention, it is preferable that the transdermal permeation rate of tolterodine (flux: $\mu g/cm^2/hr$) in a rat is adjusted in the range of 1.0-50.0 in a steady state. When the flux is less than 1.0, a sufficient drug efficacy cannot be obtained. Meanwhile, the flux of greater than 50.0 is also not preferable because a skin irritation may occur due to a rapid transfer of tolterodine into a skin. Therefore, it is preferable that the amount of the above active ingredient is determined in view of flux. Again, the amount of the tolterodine free base is 0.5-20% by weight on the basis of the total weight of the adhesive layer, and 1-10% by weight is especially preferable.

The amount of the rubber adhesive used in the adhesive layer of the tolterodine-containing patch of the present invention is 5-50% by weight, preferably 10-30% by weight on the basis of the total weight of the adhesive layer. When the amount is less than 5% by weight, the cohesive power of the adhesive layer becomes insufficient and thereby a base may be left on a skin at the time of peeling off the patch. Meanwhile, when the amount is greater than 50% by weight, the cohesive power becomes too strong, and thereby the adhesive power decreases, and further the mixing process becomes difficult.

The rubber adhesive which can be used in the adhesive layer of the tolterodine-containing patch of the present invention may be, but is not limited to, a styrene-isoprene-styrene block copolymer, a styrene-butadiene-styrene block copolymer, a styrene-ethylene-butylene-styrene block copolymer, a styrene-isoprene rubber, a polyisoprene rubber, a styrene-butadiene rubber, polyisobutylene, a chloroprene rubber, a natural rubber latex, and a SBR synthetic latex etc., and a styrene-isoprene-styrene block copolymer is especially preferable.

The styrene-isoprene-styrene block copolymer may be a commercially-available one, for example, but is not limited to, Kraton D1111, Kraton D1161, Kraton DKX401, and Kraton D1107 (trade names, Kraton Polymers Japan Ltd.), Quintac 3421 and Quintac 3570C (trade names, Zeon Corporation), SIS5002 and SIS5200 (trade names, JSR Corporation), and Cariflex TR-1107, Cariflex TR-1111, Cariflex TR-1112, and Cariflex TR-1117 (trade names, Shell Chemical Company) etc. As the styrene-isoprene-styrene block copolymer used in the patch of the present invention, a copolymer in which the polystyrene content is in the range of 10-30% by weight on the basis of the total weight of the copolymer is especially preferable. Specifically, Kraton D 1111 (polystyrene content: 22% by weight) is preferably used.

A tackifier resin is a material which is mixed with a rubber adhesive to produce adhesiveness to a skin. The amount of the tackifier resin used in the adhesive layer of the tolterodine-containing patch of the present invention is 20-60% by weight, more preferably 30-50% by weight on the basis of the total weight of the adhesive layer. When the amount of the tackifier resin is less than 20% by weight, the adhesive property of the patch becomes worse. Meanwhile, when the amount is greater than 60% by weight, the adhesive tack becomes too strong, and thereby a physical skin irritation occurs when peeling off the patch from a skin. The tackifier resin used in the present invention may be, but is not limited to, a rosin resin, an alicyclic saturated hydrocarbon resin, a terpene resin, a phenol resin, a xylene resin and the like, and they can be used alone or in a combination of two or more of them.

Rosin is a natural resin which contains mainly rosin acid obtainable by distilling a pine resin as the main ingredient. The rosin resin used in the present invention may be, but is not limited to, PINECRYSTAL KE-311, PINECRYSTAL KE-100, and ESTER GUM H (trade names, Arakawa Chemical Industries, Ltd.) etc., and FORAL 85, and FORAL 105 (trade names, Hercules Co., Ltd.) etc. The alicyclic saturated hydrocarbon resin used in the present invention may be, but is not limited to, ALCON P-70, ALCON P-90, ALCON P-100, ALCON P-115, and ALCON P-125 (trade names, Arakawa Chemical Industries, Ltd.) etc. The terpene resin used in the present invention may be, but is not limited to, YS Resin PX1150, and YS Polyster (trade names, Yasuhara Chemical Co., Ltd.), and PICCOLYTE (trade name, Hercules Co., Ltd.) etc. The phenol resin used in the present invention may be, but is not limited to, TAMANOL (trade name, Arakawa Chemical Industries, Ltd.) etc. As the tackifier resin used in the patch of the present invention, a rosin resin such as hydrogenated rosin glycerol ester, and an alicyclic saturated hydrocarbon resin are especially preferable.

The adhesive layer in the patch of the present invention may further contain a softener, for example, a fat/oil such as liquid paraffin or vaseline, and a liquid rubber such as polybutene, polyisobutylene, or polyisoprene, etc., and the amount is 5-70% by weight, more preferably 20-60% by weight on the basis of the total weight of the adhesive layer.

The liquid paraffin used in the present invention may be, but is not limited to, HICALL M-352 (trade name, KANEDA Co., Ltd.), CRYSTOL N-352 (trade name, ExxonMobil Corporation) and KAYDOL, and HYDROBRITE (Sonneborn Inc.) etc. The polybutene used in the present invention may be, but is not limited to, NISSEKI POLYBUTENE HV-300F (trade name, Nippon Petrochemicals Co., Ltd.) etc. The polyisobutylene used in the present invention may be, but is not limited to, Oppanol B-3, Oppanol B-10, Oppanol B-15, Oppanol B-50, Oppanol B-100, and Oppanol B-200 (trade names, BASF), and TETRAX 3T, TETRAX 4T, TETRAX 5T, and TETRAX 6T (trade names, Nippon Petrochemicals Co., Ltd.) etc. As the softener used in the patch of the present invention, liquid paraffin and polybutene are especially preferable.

The patch of the present invention may further contain a transdermal absorption enhancer etc. in order to enhance the transdermal absorbability of tolterodine, and the amount is normally in the range of 0.5-10% by weight on the basis of the total weight of the adhesive layer.

The transdermal absorption enhancer used in the present invention may be, but is not limited to, a fatty acid ester such as isopropyl myristate or diisopropyl adipate, a higher fatty acid such as isostearic acid, oleic acid, or myristic acid, an amine such as diisopropanolamine, or triethanolamine, or a surfactant such as a sorbitan monooleate, or lauromacrogol, or the like. Especially, isopropyl myristate is preferable.

Further, in the patch of the present invention, in order to improve the patch stability, and especially to suppress the production of a degradation product, a multivalent metal salt is preferably added. The multivalent metal salt may be, for example, zinc oxide, aluminum oxide, aluminum hydroxide, iron oxide, titanium dioxide or the like, and zinc oxide and aluminum hydroxide are used especially preferable. The amount of the multivalent metal salt is preferably 0.1-2.0% by weight on the basis of the total weight of the adhesive layer, and 0.1-0.5% by weight is especially preferable.

Further, as an adhesive base ingredient in the patch of the present invention, an additional ingredient which is usually used in a patch may be appropriately selected and used in order to adjust the base adhesiveness/stability, if necessary. For example, a water-soluble polymer such as polyvinylpyrrolidone, or polyvinyl alcohol, a cellulose derivative such as ethylcellulose, hydroxypropylcellulose, or hydroxypropyl methylcellulose, a silicon compound such as anhydrous silicic acid or light anhydrous silicic acid, an inorganic filler such as a silica, an antioxidant such as dibutylhydroxytoluene, or the like may be appropriately contained in an appropriate amount. Further, if necessary, a preservative, an algefacient, a fungicide, a flavoring agent, a colorant, or the like can be contained in the adhesive base of the present invention.

The backing in the patch of the present invention is not limited, and a normally-used elastic or non-elastic backing for patch can be used. Specifically, a film or sheet composed of a synthetic resin such as polyethylene terephthalate, polyethylene, polypropylene, polybutadiene, an ethylene-vinyl acetate copolymer, polyvinyl chloride, polyester, nylon, or polyurethane, or a laminate thereof, a porous membrane, a foam, a woven fabric, a non-woven fabric, or a paper material can be used.

In a tolterodine-containing patch product of the present invention, the adhesive layer laminated on said backing is covered by a release liner, and said release liner is peeled off when using the patch to apply the adhesive layer side to a target skin.

The release liner used in the patch of the present invention is a normally-used liner for patch, and may be, for example, polyethylene terephthalate, polypropylene, a paper, or the like, and especially polyethylene terephthalate is preferable. The release liner may be siliconized if necessary in order to optimize the release force.

Also, a deoxidant may be coexistent with the patch of the present invention in order to enhance the active ingredient stability during storage. A deoxidant made from iron or a non-ferrous metal is preferably used. When a deoxidant is coexistent with the patch, the deoxidant is directly included in a packaging container, or a deoxygenation film is laminated in a packaging container.

As an example, the patch of the present invention can be prepared by the following method. Tolterodine is dissolved in an appropriate solvent to prepare a drug solution. Separately, a styrene-isoprene-styrene block copolymer as the rubber adhesive, liquid paraffin, a tackifier resin, and other ingredients are mixed and dissolved in an appropriate solvent to obtain an adhesive base. As the solvent, toluene, ethyl acetate, ethanol, methanol or the like can be appropriately selected and used alone or in a combination of two or more of them. Subsequently, to the adhesive base is added the drug solution, the mixture is stirred and mixed to obtain a homogenous adhesive solution, the solution is spread on a release liner or a backing, the solvent is dried and removed, and then a backing or a release liner is applied thereto to obtain the patch of the present invention. The thickness of the adhesive layer is 30-200 μm, more preferably 50-100 μm. When the thickness is less than 30 μm, the drug release is not sustained. Meanwhile, the thickness is greater than 200 μm, the drug content in the adhesive layer increases, the residual drug therein increases, and the manufacturing cost increases.

Hereinafter, although the present invention is more specifically described by means of Examples, the present invention is not limited to the following Examples. Unless otherwise specified, the concentration in Examples is "% by weight". Also, in Examples and Comparative Example, the styrene-isoprene-styrene block copolymer is Kraton D1111 (Kraton Polymers Japan Ltd.), the hydrogenated rosin glycerol ester is PINECRYSTAL KE-311 (Arakawa Chemical Industries, Ltd.), the alicyclic saturated hydrocarbon resin is Alcon P-100 (Arakawa Chemical Industries, Ltd.), and the liquid paraffin is HICALL M-352 (KANEDA Co., Ltd.).

EXAMPLES

Example 1

A tolterodine free base was dissolved in toluene to prepare a drug solution. Separately, a styrene-isoprene-styrene block copolymer, liquid paraffin, and a tackifier resin were mixed and dissolved in toluene to obtain an adhesive base. To the adhesive base was added the drug solution, the mixture was stirred and mixed to obtain a homogenous adhesive solution, the solution was spread on a release liner, the solvent was dried and removed to form an adhesive layer with the thickness of 100 μm, and then a backing was applied thereto to obtain a patch. The ratio of each ingredient is shown in Table 1.

Examples 2-10

Using the ingredients shown in Table 1, according to the process in Example 1, a patch of each Example was prepared.

Examples 11-12

Tolterodine tartrate was dissolved in diethanolamine and toluene to prepare a drug solution. Then, using the ingredients shown in Table 1, according to the process in Example 1, a patch of each Example was prepared. In these formulations, it is considered that tolterodine tartrate is converted by diethanolamine and is present in the form of a free base in the adhesive base.

TABLE 1

| Ingredient (% by weight) | Ex. 1 | Ex. 2 | Ex. 3 | Ex. 4 |
|---|---|---|---|---|
| Tolterodine free base | 1 | 3 | 5 | 3 |
| Styrene-isoprene-styrene block copolymer | 17 | 17 | 17 | 17 |
| Hydrogenated rosin glycerol ester | 50 | 50 | 50 | — |
| Alicyclic saturated hydrocarbon resin | — | — | — | 50 |
| Liquid paraffin | 32 | 30 | 28 | 30 |
| Total | 100 | 100 | 100 | 100 |

| Ingredient (% by weight) | Ex. 5 | Ex. 6 | Ex. 7 | Ex. 8 | Ex. 9 | Ex. 10 |
|---|---|---|---|---|---|---|
| Tolterodine free base | 3 | 5 | 7 | 9 | 9 | 9 |
| Styrene-isoprene-styrene block copolymer | 15.7 | 16.6 | 16.3 | 16.0 | 17.0 | 17.0 |

TABLE 1-continued

| Ingredient | | | | | | |
|---|---|---|---|---|---|---|
| Hydrogenated rosin glycerol ester | — | — | — | — | — | — |
| Alicyclic saturated hydrocarbon resin | 46.1 | 49.0 | 47.9 | 46.9 | 48.0 | 48.0 |
| Liquid paraffin | 27.7 | 29.4 | 28.8 | 28.1 | 25.5 | 25.5 |
| Isopropyl myristate | 7.5 | — | — | — | — | — |
| Zinc oxide | — | — | — | — | 0.5 | — |
| Aluminum hydroxide | — | — | — | — | — | 0.5 |
| Total | 100 | 100 | 100 | 100 | 100 | 100 |

| Ingredient (% by weight) | Ex. 11 | Ex. 12 |
|---|---|---|
| Tolterodine tartrate | 4.4 | 4.4 |
| (in terms of free base) | (3) | (3) |
| Styrene-isoprene-styrene block copolymer | 16.6 | 16.4 |
| Hydrogenated rosin glycerol ester | 48.8 | 48.3 |
| Alicyclic saturated hydrocarbon resin | — | — |
| Liquid paraffin | 29.2 | 29 |
| Diethanolamine | 1 | 1.9 |
| Total | 100 | 100 |

Comparative Example

Tolterodine tartrate was suspended in toluene to prepare a drug solution. Separately, a styrene-isoprene-styrene block copolymer, liquid paraffin, and a tackifier resin were mixed and dissolved in toluene to obtain an adhesive base. To the adhesive base was added the drug solution, the mixture was stirred and mixed to obtain a homogenous adhesive solution, the solution was spread on a release liner, the solvent was dried and removed to form an adhesive layer with the thickness of 100 μm, and then a backing was applied thereto to obtain a patch. The ratio of each ingredient is shown in Table 2. In this formulation, since a basic compound is not contained, it is considered that tolterodine is not converted into a free base, and is present in the form of an acid addition salt (tolterodine tartrate) in the adhesive base.

TABLE 2

| Ingredient (% by weight) | Comp. |
|---|---|
| Tolterodine tartrate | 4.4 |
| (in terms of free base) | (3) |
| Styrene-isoprene-styrene block copolymer | 16.7 |
| Hydrogenated rosin glycerol ester | 49.3 |
| Liquid paraffin | 29.6 |
| Total | 100 |

Test Example 1

In Vitro Hairless Rat Skin Permeability Test in a Hairless Rat

In order to study the transdermal absorbability of tolterodine in the patch of the present invention, in vitro skin permeability test in a hairless rat was conducted on each Example and Comparative Example. An excised abdominal skin of hairless rat (HWY series, 7 weeks old) was put in a Franz diffusion cell, and each test formulation cut into a round shape (Φ 14 mm) was applied thereto. The receptor side was filled with phosphate buffered saline, and hot water of 37° C. was circulated in the water jacket. The receptor solution was sampled with time, and the amount of tolterodine permeated the skin was measured by a liquid chromatography. Using the result, the transdermal permeation rate (flux: μg/cm$^2$/hr) in the steady state (at 15-18 hours after the start of the test) was calculated.

The result is shown in Table 3.

TABLE 3

| Ex./Comp. | Tolterodine (% by weight) | Cumulative amount of permeated drug after 24 hours (μg/cm$^2$) | Drug permeation rate in steady state (μg/cm$^2$/h) |
|---|---|---|---|
| Ex. 1 | 1 | 21.2 | 1.10 |
| Ex. 2 | 3 | 70.2 | 4.31 |
| Ex. 3 | 5 | 130.8 | 7.98 |
| Ex. 4 | 3 | 150.7 | 8.80 |
| Ex. 5 | 3 | 177.3 | 11.21 |
| Ex. 6 | 5 | 279.4 | 13.62 |
| Ex. 7 | 7 | 354.3 | 18.63 |
| Ex. 8 | 9 | 423.7 | 21.93 |
| Ex. 9 | 9 | 426.0 | 22.75 |
| Ex. 10 | 9 | 394.2 | 21.12 |
| Ex. 11 | 3 | 29.2 | 2.04 |
| Ex. 12 | 3 | 77.2 | 4.68 |
| Comp. | 3 | 1.6 | 0.24 |

The above each test result, especially the comparison of the patch of the present invention with the patch of Comparative Example containing the same concentration of active ingredient, proves that the patch of the present invention shows an excellent transdermal absorbability as compared to the patch of Comparative Example.

Test Example 2

Tolterodine Stability Test in Formulation 1 (Content Test)

6.25 cm$^2$ of a formulation in Example 8 stored at 60° C. for 1 month was used, removed from the release liner, cut into small pieces, then put into a brown centrifuge tube containing 6 mL of tetrahydrofuran/methanol mixture (3:2), subjected to an ultrasonic irradiation for 30 minutes, and vigorously shaken up for additional 30 minutes. An extract was separated, to the residue was added 6 mL of tetrahydrofuran/methanol mixture, subjected to an ultrasonic irradiation for 30 minutes, and vigorously shaken up for additional 30 minutes. An extract was separated, and tetrahydrofuran/methanol mixture was added thereto to obtain an exactly 25 mL of solution (sample stock solution). 5 mL of this solution was exactly measured out, the mobile phase A was added thereto to obtain an exactly 25 mL of solution. This solution was filtered through a membrane filter having a pore size of 0.45 μm, and the initial 3 mL of the filtrate was removed to obtain a filtrate as a sample solution. Separately, about 14.6 mg of tolterodine tartrate standard preparation (about 10 mg in terms of tolterodine free base) was precisely weighed out, and ion-exchanged water was added thereto to obtain an exactly 20 mL of solution. 4 mL of this solution was exactly measured out, and ion-exchanged water was added thereto to obtain an exactly 10 mL of solution. 2 mL of this solution was exactly measured out, the mobile phase A was added thereto to obtain an exactly 10 mL of solution as a standard solution. Each 40 μL of the sample solution and the standard solution was measured by a liquid chromatography under the following condition to determine the peak areas $A_T$ and $A_S$ of tolterodine, and the tolterodine content in the formulation was calculated using the following formula.

$$\text{Tolterodine } (C_{22}H_{31}NO) \text{ content in sample (mg)} = W_S \times (A_T/A_S)/2 \qquad \text{[Formula 1]}$$

$W_S$: Weighed amount of tolterodine standard preparation (in terms of tolterodine free base) (mg)
$A_T$: Peak area of sample solution
$A_S$: Peak area of standard solution
Test Condition
Detector: Ultraviolet absorptiometer (measurement wavelength: 234 nm)
Column: Stainless tube having the inner diameter of 4.6 mm and the length of 25 cm filled with 5 μm of octadecylsilanized silica gel for liquid chromatography
Column temperature: Constant temperature about 40° C.
Mobile phase A: 1000 mL of solution prepared by dissolving 400 mL of acetonitrile and 10 mL of phosphoric acid in water
Flow rate: 0.85 mL/min (retention time of tolterodine: about 8 minutes)
Time span for measuring area: 12 minutes The test result is shown in Table 4. The patch of the present invention was confirmed to be a formulation with high stability.

TABLE 4

| Test formulation | Example 8 |
|---|---|
| Versus initial content (%) | 97.1 |

Test Example 3

Tolterodine Stability Test in Formulation 2 (Purity Test)

6.25 cm² of each formulation of Examples 8-10 stored at 40° C. for 2 months and Example 8 stored at 60° C. for 1 month was used, removed from the release liner, cut into small pieces, then put into a brown centrifuge tube containing 6 mL of tetrahydrofuran/methanol mixture (3:2), subjected to an ultrasonic irradiation for 30 minutes, and vigorously shaken up for additional 30 minutes. An extract was separated, to the residue was added 6 mL of tetrahydrofuran/methanol mixture, subjected to an ultrasonic irradiation for 30 minutes, and vigorously shaken up for additional 30 minutes. An extract was separated, tetrahydrofuran/methanol mixture was added thereto to obtain an exactly 25 mL of solution (sample stock solution). 5 mL of this solution was exactly measured out, and the mobile phase [mobile phase A/mobile phase B (4:1)] was added thereto to obtain an exactly 10 mL of solution. This solution was filtered through a membrane filter having a pore size of 0.45 μm, and the initial 3 mL of the filtrate was removed to obtain a filtrate as a sample solution. Each 25 μL of this solution was exactly collected and measured by a liquid chromatography under the following condition, and each peak area was determined by automatic integration method.
Test Condition
Detector: Ultraviolet absorptiometer (measurement wavelength: 234 nm)
Column: Stainless tube having the inner diameter of 4.6 mm and the length of 25 cm filled with 5 μm of octadecylsilanized silica gel for liquid chromatography
Column temperature: Constant temperature about 40° C.
Mobile phase A: 1000 mL of solution prepared by dissolving 5 mL of phosphoric acid in water
Mobile phase B: Acetonitrile
Solution sending of mobile phase: Concentration gradient control with varying mixture ratio of mobile phase A and mobile phase B as shown in the following Table 5

TABLE 5

| Time after injection (minute) | Mobile phase A (volume %) | Mobile phase B (volume %) |
|---|---|---|
| 0-60 | 80→40 | 20→60 |
| 60-60.1 | 40→10 | 60→90 |
| 60.1-75 | 10 | 90 |
| 75-75.1 | 10→80 | 90→20 |
| 75.1-100 | 80 | 20 |

Flow rate: 1.0 mL/min (retention time of tolterodine: about 22 minutes)
Time span for measuring area: 60 minutes The total amount of the degradation products in the formulation is shown in Table 6. The total amount of the degradation products is shown by the total of the ratios (%) of the peak area of each degradation product to the peak area of the active ingredient. The result in Table 6 proves that the patch of the present invention suppresses the production of degradation products under each storage condition. Especially, regarding the formulations in Example 9 and Example 10 containing a multivalent metal salt, the production of the degradation products was suppressed.

TABLE 6

| | Storage condition | |
|---|---|---|
| Test formulation | 60° C./1 month | 40° C./2 months |
| Example 8 | 0.96 | 0.40 |
| Example 9 | — | 0.24 |
| Example 10 | — | 0.29 |

Unit: Total amount of degradation products (%)

Test Example 4

Skin Primary Irritation Test in a Rabbit

Using each formulation in Example 6 and Example 8, a skin primary irritation test in a rabbit was carried out. Each patch was applied onto a dehaired rabbit back for 48 hours, and Primary Irritation Index (P.I.I) was determined by the skin symptom at 1 hour, 24 hours and 48 hours after peeling off. The result and the evaluation criteria are shown in Table 7 and Table 8 respectively.

TABLE 7

| (Result) | | |
|---|---|---|
| Test formulation | Example 6 | Example 8 |
| Primary Irritation Index (P.I.I) | 1.63 | 2.17 |

TABLE 8

| (Evaluation criteria) | |
|---|---|
| P.I.I | Safety classification |
| P.I.I = 0 | Non irritant |
| 0 < P.I.I < 2 | Mild irritant |

TABLE 8-continued (Evaluation criteria)

| P.I.I | Safety classification |
|---|---|
| 2 ≤ P.I.I < 5 | Moderate irritant |
| 5 ≤ P.I.I | Severe irritant |

The result in Table 7 proves that the skin irritation caused by the patch of the present invention is low.

INDUSTRIAL APPLICABILITY

According to the present invention, a tolterodine-containing patch in which the transdermal absorbability and the stability of tolterodine are excellent, and the skin irritation is low can be provided.

The invention claimed is:

1. A tolterodine-containing patch consisting of an adhesive layer, a backing, and a release liner, the adhesive layer consisting of tolterodine as an active ingredient, a rubber adhesive that is a styrene-isoprene-styrene block copolymer, one or more tackifier resins that are hydrogenated rosin glycerol ester or an alicyclic saturated hydrocarbon resin, a softener that is liquid paraffin, optionally a transdermal absorption enhancer that is isopropyl myristate, optionally a multivalent metal salt that is zinc oxide or aluminum hydroxide, and optionally a basic compound that is diethanolamine, wherein the tolterodine is present in the form of a free base in the adhesive base, and wherein the adhesive layer is laminated on the backing.

2. The patch according to claim 1, wherein the amount of the tolterodine free base is in the range of 0.5-20% by weight on the basis of the total weight of the adhesive layer.

3. The patch according to claim 1, wherein the amount of the tolterodine free base is in the range of 1-10% by weight on the basis of the total weight of the adhesive layer.

4. The patch according to claim 1, wherein the amount of the rubber adhesive is in the range of 5-50% by weight on the basis of the total weight of the adhesive layer.

5. The patch according to claim 1, wherein the polystyrene amount in the styrene-isoprene-styrene block copolymer is in the range of 10-30% by weight on the basis of the total weight of the copolymer.

6. The patch according to claim 2, wherein the amount of the rubber adhesive is in the range of 5-50% by weight on the basis of the total weight of the adhesive layer.

7. The patch according to claim 3, wherein the amount of the rubber adhesive is in the range of 5-50% by weight on the basis of the total weight of the adhesive layer.

8. The patch according to claim 1, wherein the transdermal permeation rate of tolterodine in a steady state is in the range of 1.0-50.0 µg/cm$^2$/hr.

9. The tolterodine-containing patch of claim 1, wherein the tolterodine is present in an amount of 0.5% to 20% by weight, the rubber adhesive is present in an amount of 5% to 50% by weight, the tackifier resins are present in an amount of 20% to 60% by weight, the softener is present in an amount of 5% to 70% by weight, optionally the transdermal absorption enhancer is present in an amount of 0.5% to 10% by weight, optionally the multivalent metal salt is present in an amount of 0.1% to 2.0% by weight, and optionally the basic compound is present in an amount of 0.3% to 13% by weight.

10. The tolterodine-containing patch of claim 9, wherein the tolterodine is present in an amount of 1% to 10% by weight, the rubber adhesive is present in an amount of 10% to 30% by weight, the tackifier resins are present in an amount of 30% to 50% by weight, the softener is present in an amount of 20% to 60% by weight, optionally the multivalent metal salt is present in an amount of 0.1% to 0.5% by weight, and optionally the basic compound is present in an amount of 0.6% to 6.5% by weight.

11. A tolterodine-containing patch consisting of an adhesive layer, a backing, and a release liner, the adhesive layer consisting of tolterodine as an active ingredient, a rubber adhesive, one or more tackifier resins, a softener, optionally a transdermal absorption enhancer selected from the group consisting of a fatty acid ester, a higher fatty acid, an amine, sorbitan monooleate, and lauromacrogol, optionally a multivalent metal salt, optionally a basic compound, optionally a water-soluble polymer, optionally a cellulose derivative, optionally a silicon compound, optionally an inorganic filler, optionally an antioxidant, optionally a preservative, optionally an algefacient, optionally a fungicide, optionally a flavoring agent, and optionally a colorant, wherein the tolterodine is present in the form of a free base in the adhesive base, and wherein the adhesive layer is laminated on the backing.

12. The patch according to claim 11, wherein:
the rubber adhesive is selected from the group consisting of a styrene-isoprene-styrene block copolymer, a styrene-butadiene-styrene block copolymer, a styrene-ethylene-butylene-styrene block copolymer, a styrene-isoprene rubber, a polyisoprene rubber, a styrene-butadiene rubber, polyisobutylene, a chloroprene rubber, a natural rubber latex, and a SBR synthetic latex;
the tackifier resins are selected from the group consisting of a rosin resin, an alicyclic saturated hydrocarbon resin, a terpene resin, a phenol resin, and a xylene resin;
the softener is selected from the group consisting of a fat/oil and a liquid rubber;
the multivalent metal salt is selected from the group consisting of zinc oxide, aluminum oxide, aluminum hydroxide, iron oxide, and titanium dioxide;
the basic compound is selected from the group consisting of sodium hydroxide and an amine;
the water-soluble polymer is selected from the group consisting of polyvinylpyrrolidone and polyvinyl alcohol;
the cellulose derivative is selected from the group consisting of ethylcellulose, hydroxypropylcellulose, and hydroxypropyl methylcellulose;
the silicon compound is selected from the group consisting of anhydrous silicic acid and light anhydrous silicic acid;
the inorganic filler is a silica; and
the antioxidant is dibutylhydroxytoluene.

13. The patch according to claim 12, wherein:
the rubber adhesive is a styrene-isoprene-styrene block copolymer;
the tackifier resins are hydrogenated rosin glycerol ester or an alicyclic saturated hydrocarbon resin;
the softener is liquid paraffin;
the transdermal absorption enhancer is isopropyl myristate;
the multivalent metal salt is zinc oxide or aluminum hydroxide; and
the basic compound is diethanolamine.

* * * * *